(12) United States Patent
Plecis

(10) Patent No.: US 8,715,475 B2
(45) Date of Patent: May 6, 2014

(54) MICROFLUIDIC DEVICE FOR SEPARATING, FRACTIONATING, OR PRECONCENTRATING ANALYTES CONTAINED IN AN ELECTROLYTE

(75) Inventor: Adrien Plecis, Vert-le-Petit (FR)

(73) Assignee: Etat Francais Represente Par le Delegue General pour l'Armement, Armees (FR)

( * ) Notice: Subject to any disclaimer, the term of this patent is extended or adjusted under 35 U.S.C. 154(b) by 402 days.

(21) Appl. No.: 13/127,113

(22) PCT Filed: Nov. 3, 2009

(86) PCT No.: PCT/FR2009/001273
§ 371 (c)(1),
(2), (4) Date: Jul. 22, 2011

(87) PCT Pub. No.: WO2010/052387
PCT Pub. Date: May 14, 2010

(65) Prior Publication Data
US 2011/0272281 A1 Nov. 10, 2011

(30) Foreign Application Priority Data
Nov. 4, 2008 (FR) .................................. 08 06137

(51) Int. Cl.
*G01N 27/447* (2006.01)
*G01N 27/453* (2006.01)

(52) U.S. Cl.
USPC .......................................... 204/454; 204/601

(58) Field of Classification Search
USPC ........................... 204/601–602; 205/451–454
See application file for complete search history.

(56) References Cited

U.S. PATENT DOCUMENTS

| 5,151,164 | A | 9/1992 | Blanchard et al. |
| 5,358,618 | A | 10/1994 | Ewing et al. |
| 7,081,189 | B2 * | 7/2006 | Squires et al. ................ 204/451 |
| 2002/0079219 | A1 | 6/2002 | Zhao et al. |
| 2009/0008255 | A1 | 1/2009 | Class et al. |

FOREIGN PATENT DOCUMENTS

| DE | 10 2006 004 887 A1 | 8/2007 |
| EP | 1 362 827 A1 | 11/2003 |
| WO | WO 00/60341 A1 | 10/2000 |
| WO | WO 2009061843 A2 * | 5/2009 ............... C12Q 1/68 |

OTHER PUBLICATIONS

Rifafi et al., "Ability of porous graphitic carbon to support electrosomotic flow in capillary electrochromatography," Journal of Chromatography A, 973 (2002) 177-186.*

(Continued)

*Primary Examiner* — Alex Noguerola
(74) *Attorney, Agent, or Firm* — Oliff PLC

(57) ABSTRACT

A microfluidic device for separating, fractionating, or preconcentrating analytes contained in an electrolyte having at least two reservoirs separated by at least one microchannel and/or nanochannel. At least part of the wall of the microchannel is made of and/or coated interiorly with a conducting and polarizable material or group of materials constituting a polarizable interface or a network of polarizable interfaces. In that at least one electrode or at least one electrode network is connected at at least one point of the polarizable material or group of materials, the surface electrical conductance of said material being equal to at least 100 nS.

11 Claims, 19 Drawing Sheets

(56) References Cited

OTHER PUBLICATIONS

Sniadecki et al., "Induced pressure pumping in polymer microchannels via field-effect flow control," *Analytical Chemistry*, 2004, vol. 76, No. 7, pp. 1942-1947.

Mpholo et al., "Low voltage plug flow pumping using anisotropic electrode arrays," *Sensors and Actuators*, 2003, vol. 92, pp. 262-268.

Kim et al., "A disposable capillary electrophoresis microchip with an indium tin oxide decoupler/amperometric detector," *Microelectronic Engineering*, Elsevier Publishers, 2005, vol. 78, pp. 563-570.

Chien-Hsien Wu et al., "Electrokinetically driven flow control using bare electrodes," *Microfluid Nanofluid*, 2007, vol. 3, pp. 485-494.

Huang, "The principles of separation in CE," *Chromatographia Supplement*, 2001, vol. 54, No. 9, pp. 15-23.

Plecis et al., "Electropreconcentration with charge-selective nanochannels," *Analytical Chemistry*, 2008, vol. 80, No. 24, pp. 9542-9550.

Schasfoort et al., "Field-effect flow control for microfabricated fluidic networks," *Science*, 1999, vol. 286, pp. 942-945.

Karnik et al., "Field-effect control of protein transport in a nanofluidic transistor circuit," *Applied Physics Letters*, 2006, vol. 88, pp. 1-3.

McDonald et al., "Poly(dimethylsiloxane) as a material for fabricating microfluidic devices," *Accounts of Chemical Research*, 2002, vol. 35, No. 7, p. 491-499.

Plecis et al., "Fabrication of microfluidic devices based on glass-PDMS-glass technology," *Microelectronic Engineering*, 2007, vol. 84, pp. 1265-1269.

Plecis et al., "Microfluidic analogy of the wheatstone bridge for systematic investigations of electro-osmotic flows," *Analytical Chemistry*, ACS Publications, vol. 80, No. 10, pp. 3736-3742.

International Search Report issued in International Patent Application No. PCT/FR2009/001273 dated Mar. 30, 2010 (with translation).

International Preliminary Report on Patentability issued in International Patent Application No. PCT/FR2009/001273 dated Mar. 29, 2010 (with translation).

Written Opinion issued in International Patent Application No. PCT/FR2009/001273 dated Mar. 30, 2010 (with translation).

Written Opinion issued in French Patent Application No. 0806137 dated Jun. 23, 2009 (with translation).

Preliminary Search Report issued in French Patent Application No. 0806137 dated Jun. 23, 2009 (with translation).

\* cited by examiner

View from the top

View along section BB'

Geometry

Potential distributions

Current distributions

MICROFLUIDIC DEVICE FOR SEPARATING, FRACTIONATING, OR PRECONCENTRATING ANALYTES CONTAINED IN AN ELECTROLYTE

CROSS REFERENCE TO RELATED APPLICATIONS

This application is the National Stage of PCT/FR2009/001273 filed on Nov. 3, 2009, which claims priority under 35 U.S.C. §119 of French Application No. 0806137 filed on Nov. 4, 2008. The international application under PCT article 21(2) was not published in English.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

The invention relates to the field of materials research or analysis using electrical means and has as a particular subject a microfluidic device for separating, fractionating, or preconcentrating analytes contained in an electrolyte.

Surface potential is involved in many analytical separation processes. For example, microfluidic devices for separating analytes contained in an electrolyte employing capillary electrophoresis are known. This process is generally implemented by a microfluidic network into which an electrolyte and a specimen containing analytes are injected. This network may have a number of reservoirs connected to at least one long microchannel and/or to a microchannel network having intersections in a particular arrangement to enable injection of a certain quantity of analytes into the central microchannel. Application of an electric field in this same channel, known as separation channel, after the injection phase, is responsible for migration of the analytes. Under the effect of an electric field, the charged particles move in a liquid medium at a speed defined both by the field and by the mass and charge of the particles (electrophoresis). The particle speed in the liquid is proportional to the electric field, the proportionality constant being called electrophoretic mobility. At the solid-liquid wall, a double ionic layer formed of a fixed layer of ions, corresponding to the surface charge, and of a mobile ion layer, corresponding to a diffuse layer in the liquid, forms spontaneously. Under an electric field, the ions in the mobile layer migrate, bringing about a general liquid movement by viscosity (electroosmosis). The latter moves in a single block and its speed is also proportional to the electric field. The proportionality constant between the fluid speed and the electric field is called electroosmotic mobility. The concomitant action of the electrophoretic migration (speed of ions in the liquid) and the electroosmotic liquid flowrate (liquid speed) that are generated by the difference in potential acts on the ions contained in the fluid, ensuring that they are carried through the separation channel. The total speed of an ion in a microchannel subjected to an electric field is hence proportional to the electric field. The proportionality constant is the total mobility of the ion which is the sum of its electrophoretic mobility (specific to each ion) and the electroosmotic mobility (promotional to the surface potential).

The various analytes can be detected sequentially in time at the end of the long microchannel, giving information on the number of analytes present in the solution to be analyzed and their respective concentrations. This method is known for its very good resolution in separating two analytes. To achieve the highest possible separation efficiency, one must control the direction and amplitude of the electroosmotic flow (EOF). The resolution of this technique is maximal when the surface potential is such that the electroosmotic mobility is the converse of the average electrophoretic mobility of the species to be separated (see Huang, L. R., The Principles of Separation in CE, *Chromatographia Supplement*, 54 (9), pp. 15-23).

Numerous preconcentration systems also require the surface potential parameter to be controlled. French Patent Application No. FR0805264 consists of a selective preconcentration technique based on the variation in the surface charge parameter (NB: the surface charge can be expressed as surface potential and vice versa).

In nanofluidics, it is also known that the selectivity of ion transport depends on the surface potential and the preconcentration of a biological specimen with the aid of such nanometric structures depends essentially on this parameter (Plecis A., Nanteuil C., Haghiri-Gosnet A., Chen Y., "Electropreconcentration with Charge Selective Nanochannels," *Analytical Chemistry*, 2008). For all these reasons, numerous techniques have been proposed and numerous patents have been filed to control this parameter based on an external control system of the voltage source type. These techniques are known as "radial electric field" when they are applied to systems of the capillary type, or as microfluidic or nanofluidic transistors when applied to microfluidic systems (for example by Schasfoort, R. B. M., et al., Field-Effect Flow Control for Microfabricated Fluidic Networks, *Science*, 1999 or by Karnik, R, K. Castelino, and A. Majumdar, Field-Effect Control of Protein Transport in a Nanofluidic Transistor Circuit, *Applied Physics Letters*, 2006). We will now describe in detail two examples of patents inspired by these structures of the Metal/Insulator/Electrolyte (MIE) type in order to control the surface potential (also generally called "zeta" potential).

Thus, FIG. 1, from U.S. Pat. No. 5,151,164, describes a device for separation by capillary electrophoresis of analytes contained in an electrolyte, said device having two reservoirs 1, 2 separated by a capillary 3. This capillary 3 is made of a non-conducting material, for example glass, plastic, or silica. A first and a second electrode 4, 5, with which a voltage generator 6 is associated, are disposed on one and the other side respectively of the microchannel 10 and are able to generate, inside the latter, a first longitudinal electric field. A third electrode 7, disposed around capillary 3 and over almost its entire length, is able to generate a radial electric field inside the latter.

Controlling the direction and amplitude of the electroosmotic flow is achieved by controlling the voltage applied to the ends of the third electrode 7. A drop in electric potential of at least 0.4 kV is applied through this electrode, enabling a constant potential difference with the liquid in capillary 3 to be obtained and also the inside surface potential of the capillary to be controlled.

However, this sharp voltage drop in the external electrode causes a substantial Joule effect and, to avoid this drawback, U.S. Pat. No. 5,358,618 proposes using a single potential electrode positioned over a restricted length of the microchannel. This device controls electroosmotic flow while limiting heating of the liquid due to the Joule effect.

Referring to other microsystems in which the surface potential is controlled with the aid of a radial potential, all have this same configuration, known as "Metal-Insulator-Electrolyte" (MIE), which consists of insulating an electrode from the electrolyte with an insulating layer and applying a potential to this electrode that is different from the potential of the electrolyte in order to modify, by a capacitive effect, the surface potential of the insulator. FIG. 2a shows the evolution of the electric potential through an MIE structure surrounding the microchannel. FIG. 2b shows an electric modeling of this type of interface. $V_g$ corresponds to the potential applied to the metal, $\Psi$ to the Stern potential at the limit of the insulator, $\zeta$ to the zeta potential (or surface potential beyond the layer of ions adsorbed at the surface), and $\Phi$ to the liquid potential (beyond the contra-ion layer, called diffuse layer). The decrease in potential is linear in the insulator and the Stern layer, while the decrease is exponential in the diffuse layer.

If the capacitance of the Stern layer, whose value is not known at the outset, is ignored, the variation in surface potential $\zeta$ implied by an overvoltage between the liquid and the electrode $(V-\Phi)$ can be estimated:

$$\Delta\zeta = \frac{C_{insulator}}{C_{DL}}(V-\phi) = \frac{\lambda_D \varepsilon_{insulator}}{l_{insulator}\varepsilon_{liquid}}(V-\phi).$$

where $\lambda_D$ is the thickness of the diffuse layer (Debye length—see Hunter, "Zeta Potential in Colloids Science", Academic Press, London, 1981), $l_{insulator}$ is the thickness of the insulator, $\varepsilon_{insulator}$ and $\varepsilon_{liquid}$ designate respectively the electric permittivity of the insulator and of the electrolyte. The variation in potential at the liquid interface is hence proportional to the difference in potential between the liquid and the electrode. There are three main difficulties with these interfaces:

the first has to do with the fact that the potential in the liquid varies linearly along the microchannel. Hence, the induced surface potential is not homogeneous along the capillary. This phenomenon is illustrated in FIG. 3 where a channel 20 has a first electrode 21 at one of its ends and a second electrode 22 at its other end, these electrodes being connected to means 25 for generating and controlling a voltage between them. A non-conducting material 23 is provided on part of the outer face of the channel and a third electrode 24 is connected thereto. Means 26 for generating and controlling a voltage are associated with this third electrode. The inhomogeneity of the surface potential is represented by the signs – and + below the non-conducting material 23.

The second limitation derives from the proportionality factor between the applied external voltage and the surface potential difference generated. This factor is generally very small and even tends to zero when the ionic concentration increases (it is proportional to the Debye length). Thus, for a 10 mM solution, and an insulating layer of the SiO$_2$ type (2 μm thickness), a voltage difference of about 100 V has to be applied to obtain a difference of only 10 mV at the interface. Since the dielectric strength of glass does not enable electric fields greater than 8 MV/m on average to be applied for a layer 2 μm thick, the maximum permissible voltage before breakdown would a priori be 16 V, hence a maximum surface potential control of only 1.6 mV.

Finally, the third difficulty is linked to the technological near-impossibility of making a thin and truly insulating layer in a liquid medium with current microfabrication techniques. Indeed, the slightest imperfection in this layer results in a large faradaic current between the metal electrode and the liquid, which disturbs the value of the electrolyte's electric potential. This obviously must not occur in electrophoretic separation, fractionation, or preconcentration steps.

Moreover, a device according to U.S. Pat. No. 5,151,164 and U.S. Pat. No. 5,358,618 and any classical capillary electrophoresis device also has the drawback of becoming nonfunctional when a bubble, created for example by the Joule effect, is created inside the microchannel. If this happens, the bubble acts as an electrical insulator and no electric current can be established in the capillary so that any electroosmotic flow is "stopped".

To overcome this drawback, Patent application WO 00/60341 proposes using a cylindrical microchannel whose entire inside face is covered with a resistive coating such as a semiconductor polymer (polyaniline, polypyrrole, etc.), and connecting the ends of this coating to a voltage source that also allows the electric field to be imposed in the liquid part. In this case, the resistive interface conducts the current despite the presence of a bubble and the latter can be carried by the electroosmotic flow. This type of device, while it solves the problem of bubbles in capillary devices, nonetheless does not enable the surface mobility to be properly controlled.

Classical microfabrication techniques cannot be applied to this type of system and covering the entire inside face of a cylindrical microchannel homogenously is extremely difficult or even impossible to accomplish with solid materials. So, coating techniques based on hydrodynamic injection of polymer solutions are used, where the solutions are deposited passively on the inside of the capillary. This type of technique does not provide sufficient homogeneity for the surface conductivity and does not allow integration of highly conductive solid materials. Moreover, it is impossible to connect the resistive layer at points other than the ends of the capillary. Hence, the control of the electric potential in this resistive layer is strongly limited.

Furthermore, the use of the above-mentioned polymers requires strong faradaic currents between the liquid medium and the resistive layer. This electron transfer between the liquid and the resistive layer is essential in the context of the application described which consists of using the resistive layer as a "short circuit" when a bubble forms in the liquid part of the capillary. This property implies minimal polarizability at the solid-liquid interface. Moreover, the low conductivities referred to for the resistive layer mean that the potential difference between the liquid and the resistive layer cannot be maintained along the microchannel.

BRIEF SUMMARY OF THE INVENTION

The goal of the invention is to propose a microfluidic device overcoming the drawbacks of the devices described above by proposing a microfluidic device for separating, fractionating, or preconcentrating analytes contained in an electrolyte having at least two reservoirs separated by at least one planar microchannel and/or nanochannel, said device being characterized in that said at least one microchannel and/or nanochannel has a planar geometry and in that at least part of the upper and/or lower wall of the microchannel is comprised of and/or coated interiorly with a conducting and polarizable material or group of materials constituting a polarizable interface or a network of polarizable interfaces and in that at least one electrode or at least one electrode network is connected at least one point of the polarizable material or group of materials, the surface electrical conductance of said conducting and polarizable material or group of materials being equal to at least 100 nS, its polarizability window with respect to oxidation-reduction reactions involving water, OH– and H+ ions, being at least 0.5 V for the cathodic and anodic reactions and having a faradaic current less than 50 µA/cm² in this polarizability window of at least 1V in contact with an aqueous liquid such as a 0.1 M KCl solution with pH 7.

Thus, the polarizable interface is directly in contact with the liquid able to circulate inside the microchannel and its electric potential can be controlled at any point in the interface, which also allows fine control of the surface potential, almost eliminating faradaic currents. Moreover, with such a geometry, rectangular for example, it is possible to control the surface potential independently over two opposite inside faces and/or over different longitudinal portions of a given micro/nanofluidic network.

"Conducting" means that the thin layer has a surface electrical conductivity at least greater than 100 nS.

"Planar geometry" means that the microchannel section is polyhedral in shape.

"Surface electrical conductance" (expressed in S) means the volume conductance (expressed in S/m) multiplied by the height of the structured layer (expressed in m).

"Polarizable interface" means any conducting material or group of materials that has a very weak faradaic current when there is applied to it an overvoltage within a polarizability window with respect to oxidation-reduction reactions involving water, OH– and H+ ions, namely as long as the overvoltage $/V-\Phi/<V0$, where V is the potential in the polarizable interface, $\Phi$ is the equilibrium potential of the electrode with the electrolyte, and V0 is the faradaic overvoltage associated with the material-electrolyte pair. This polarizability window of the material with respect to oxidation-reduction reactions involving water, OH– and H+ ions, must be at least 1 volt with at least + or –500 mV on either side of the equilibrium potential of the interface in order for the surface potential control to be exercised significantly and must have, over the entire window, a faradaic current of less than 50 microampere per square centimeter for a 0.1M KCl solution with a pH of 7. In other words, the polarizability window of the material with respect to oxidation-reduction reactions involving water, OH– and H+ ions is at least 0.5 V for cathodic and anodic reactions and has a faradaic current less than 50 µA/cm² in this polarizability window of at least 1 V (0.5 V+0.5 V) in contact with an aqueous liquid such as a 0.1 M KCl solution with pH 7.

Among the polarizable materials meeting this definition are, in particular, conducting SiC such as SiCxHy with $x \neq 1$ and $y \neq 0$, CNx, CNxHy, pure carbon, and doped diamond. "Group of materials" means any stack or mixture of these materials.

According to one particular feature, said microchannel has n walls where n>2 and at most n–1 walls, and is coated with or comprised of a conducting and polarizable material or group of materials constituting a polarizable interface or a network of polarizable interfaces.

According to an additional feature enabling the absolute value of the zeta potential to be controlled, a device according to the invention has at least one reference electrode preferably composed of a part of the polarizable interface network not connected to this network and connected at least one point to an electrode not connected with the rest of the electrode network. This electrode is able to measure the electric potential of the electrolyte at a point in the microfluidic network and allows the zeta potential to be controlled absolutely at the polarizable interface. The system has as many reference electrodes as necessary. For example, when the potential must be controlled along a rectilinear section, a second electrode, known as a reference electrode, able to measure the potential at the other side of said microchannel, is preferably used. In general, and to the degree that the exact potential of the liquid is unknown, a reference electrode will preferably be associated with any electrode enabling the potential to be imposed at the polarizable interface. To avoid any disruptive faradaic current at the reference electrodes, it will be preferable to combine each so-called reference electrode with an electrical means known as "voltage follower" able to supply a current for a potential identical to that of the reference electrode, while guaranteeing a minimum current at the reference electrode.

According to an additional feature, a device according to the invention has at least a first and a second electrode known as "longitudinal field" electrodes with which a voltage generator is associated, these electrodes being disposed respectively on one and the other side of at least one microchannel coated with said polarizable interface and able to generate, inside the latter, a longitudinal electric field in the liquid. These electrodes can be, for example, either macroscopic electrodes placed in the reservoirs or micro-electrodes placed in the fluidic network.

According to another feature, a device according to the invention has at least first means for generating an overpressure in at least one of the reservoirs, said means being preferably also able to control the value of this overpressure. Thus, this overpressure is able to create movement in a fluid contained in the microfluidic network with the aid of a pressure gradient. The electric potential imposed at the polarizable interface can for example in this case be imposed from the potential measured with the aid of an electrode known as a reference electrode.

With such a device, the surface potential can be controlled over at least part of the microfluidic system homogenously, or, if the application so requires, inhomogeneously.

The invention also relates to a method for separating, fractionating, or preconcentrating analytes contained in an electrolyte implemented by a device according to the invention, having the following steps:

filling at least one reservoir with an electrolyte and a specimen to be analyzed that contains analytes, applying at least one potential difference between at least one longitudinal or reference electrode and at least one control electrode connected at a point in the polarizable network, applying at least one potential difference at the longitudinal electrodes and/or a pressure difference at the reservoirs, with the aid of a detector, detecting the presence of analytes at least one point of the microfluidic network.

According to an additional feature, a method according to the invention also includes at least one of the following steps:

varying the control potential difference continuously or sequentially;

varying the electric potential or pressure difference continuously or sequentially.

BRIEF DESCRIPTION OF THE SEVERAL VIEWS OF THE DRAWING

Other advantages and features will emerge from the description of specific embodiments of the invention with reference to the attached drawings, among which:

FIG. 16a shows the arrangement of a polarizable interface and its associated electrode network with a microchannel according to a third embodiment of the invention.

FIG. 16b shows the curve of the overvoltage along the microchannel of the arrangement of FIG. 16a.

DETAILED DESCRIPTION OF THE INVENTION

Figure 4A:
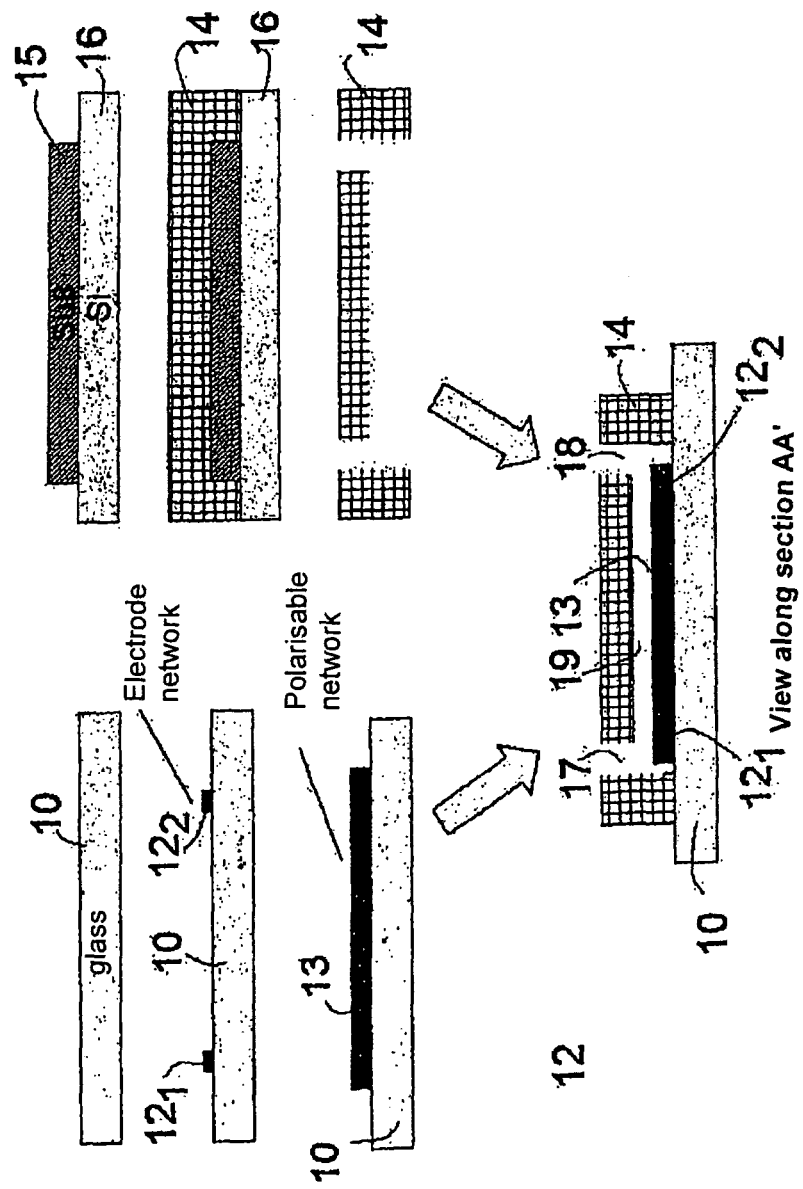
FIGS. 4a to 4c are diagrams of one exemplary embodiment of a device according to a first embodiment of the invention.
Figure 4B:
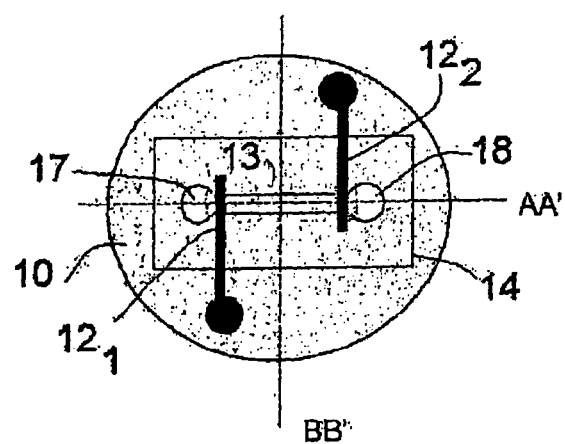
Figure 4B:
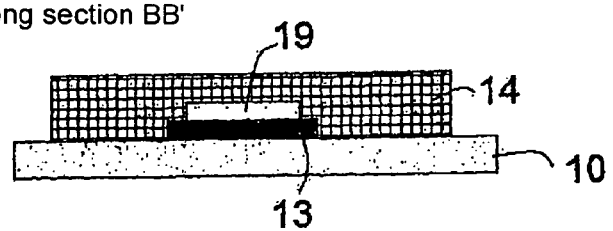

FIGS. 4a and 4b illustrate a first embodiment of the invention having a polarizable interface located on the bottom part of a rectangular microchannel created between two reservoirs with the aid of a standard technique known as glass-PDMS. FIG. 4a illustrates more precisely a layout of microstructuring steps that can be associated with implementation of the first embodiment. The device is comprised of a glass substrate 10 to 500 µm thick on which are successively structured a network of metal electrodes 12 (Ti/Pt-thicknesses 5 nm/50 nm) then a polarizable network 13, here of rectangular geometry with conducting SiC, specifically SiCxHy (thickness 100 nm). The electrode network is structured with a standard liftoff technique composed of a photolithographic step using a reversible resin of the Dow Corning AZ5214 type, a metal deposition step (by evaporation), and a development step during which the substrate is dipped in acetone, whereby dissolution of the resin releases the metal deposited thereon while the resinless regions retain the metal layer thus structured. The polarizable network is made with the aid of a magnetron radiofrequency cathodic sputtering deposition step with a conducting crystalline SiC target, specifically SiCxHy, followed by a photolithographic step using a reversible resin of the AZ5214 type that masks the pattern to be made during the following step of fluorinated plasma etching. The resin is then dissolved in acetone to obtain the fully structured lower substrate.

The microchannels are made from a block of polydimethylsiloxane (PDMS) 14 with the aid of a casting technique described in particular by McDonald (McDonald, J. C. and G. M. Whitesides, Poly(dimethylsiloxane) as a Material for Fabricating Microfluidic Devices, *Accounts of Chemical Research,* 2002, 35(7): pp. 491-499). Here, a photosensitive resin (SU8) 15 is used to make the microfluidic network as a "negative" on a silicon substrate 16. A casting step then consists of pouring liquid PDMS (base polymer+crosslinking agent) onto the mold then causing it to crosslink at room temperature or at a temperature of about 75° C. to speed up the crosslinking step, then separating the microfluidic network thus cast in the PDMS of the original mold. After punching reservoirs 17, 18 out of the PDMS block with the aid of a punch, the lower substrate and the PDMS block are exposed to a short oxygen plasma (typically 30 sec) to activate the surface groups. When the two surfaces are brought into contact (after alignment), a covalent bond operates between them and the microfluidic network is thus finalized.

Thus a microchannel 19 with a rectangular section is obtained of which a single inside face 20 is composed of a polarizable network (FIG. 4b). The metal electrodes $12_1, 12_2$ enable an electric potential to be imposed at each end of the polarizable interface. For this purpose, an electric potential source 21 is connected to the "connecting zones" of the electrode network located outside the microfluidic network. In order for the potential drop to be minimal in the electrode network, it is important to preserve a sufficient surface conductivity ratio between the electrode network and the polarizable interface network (at least >10 and preferably about 1000).

Figure 4C:
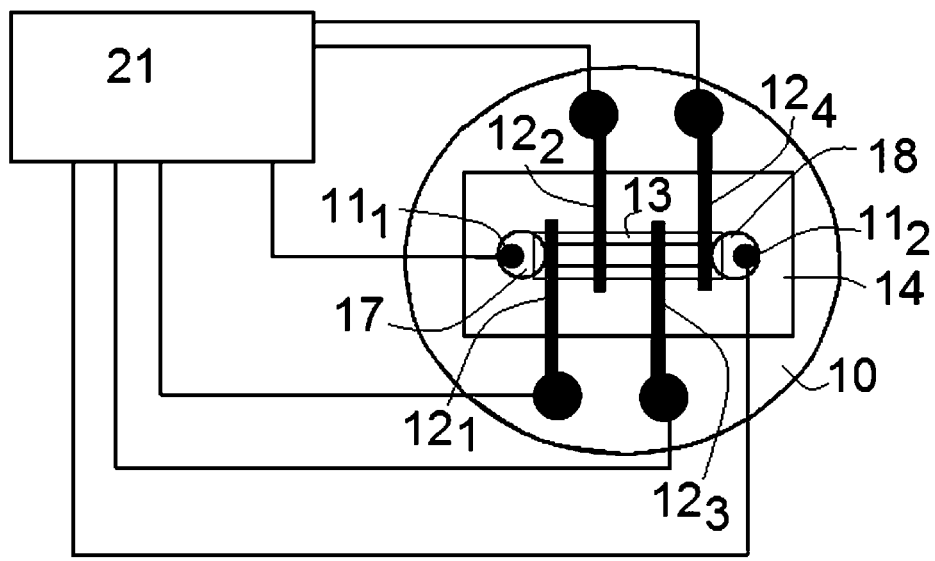

FIG. 4c shows a second embodiment equivalent to that of FIGS. 4a and 4b in which several control electrodes $12_1$, $12_2$, $12_3$, $12_4$ are connected to the polarizable interface. It also shows the multiple voltage source 21 that controls the interface potential at these various contact points. The multiple voltage source is moreover connected to two electrodes $11_1$, $11_2$ made of macroscopic platinum placed in reservoirs 17, 18 and enabling the potential of the liquid to be controlled.

Figure 1:
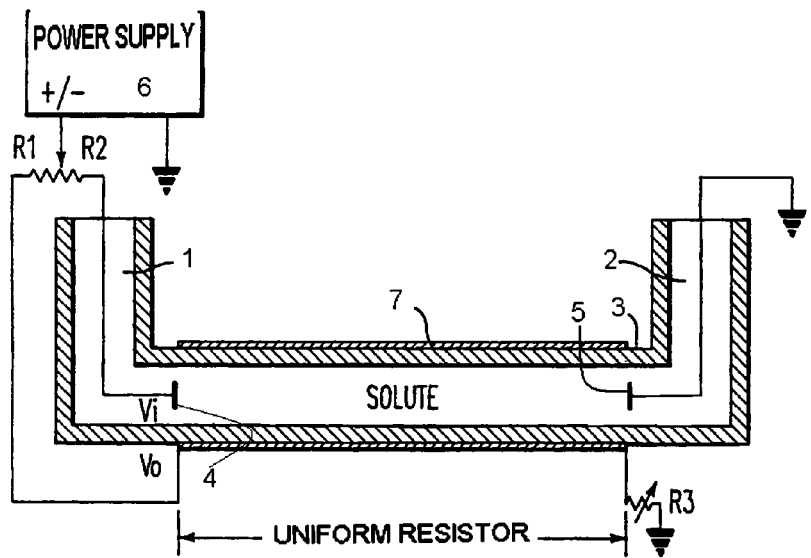
FIG. 1 describes a prior art device for separation by capillary electrophoresis of analytes contained in an electrolyte.
Figure 2A:
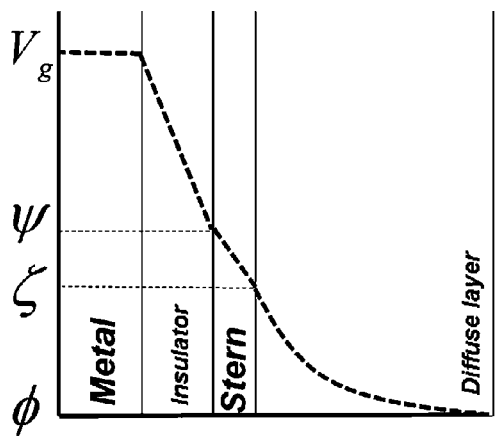
FIG. 2a shows the evolution of the electric potential through an MIE structure surrounding a microchannel and FIG. 2b shows an electric modeling of this type of interface.
Figure 2B:
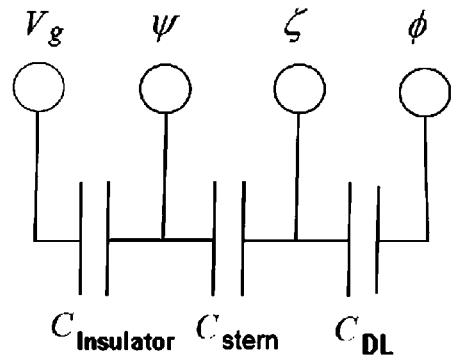
Figure 3:
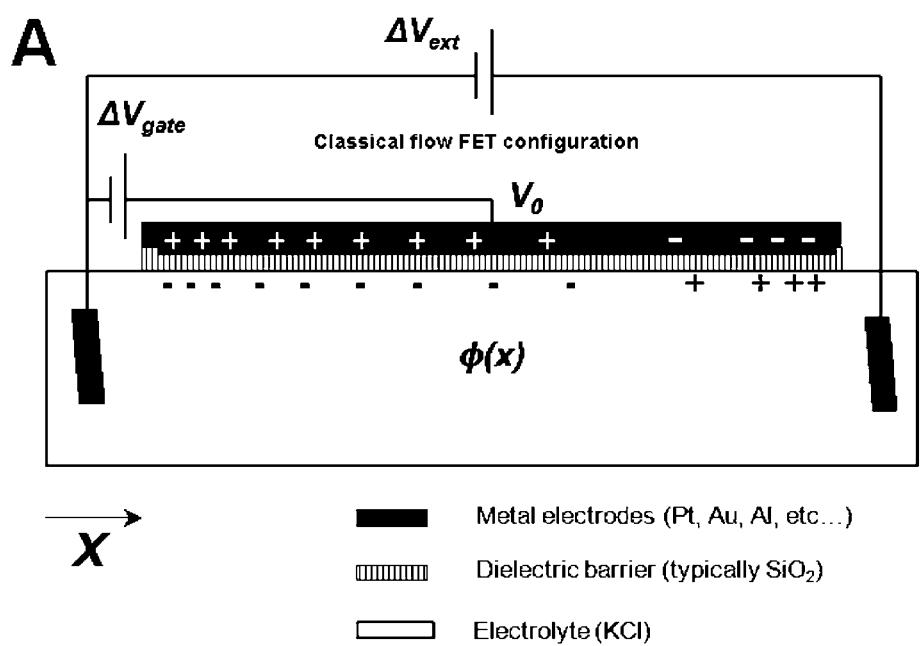
FIG. 3 illustrates a phenomenon where induced surface potential is not homogeneous along a capillary.
Figure 5:
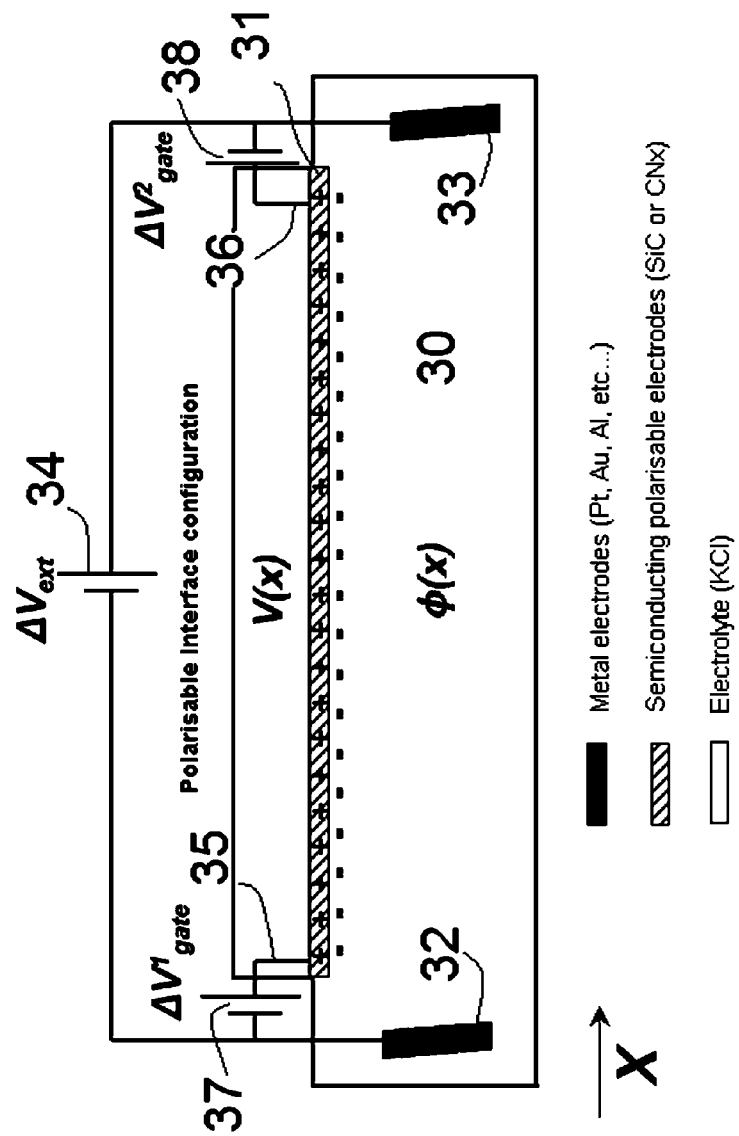
FIG. 5 is a diagram illustrating, at one polarizable interface, the surface potential in the context of a device according to the invention.

FIG. 5 is a diagram showing, at a polarizable interface, the surface potential in the context of a device according to the invention. This figure corresponds to the embodiment described in FIGS. 4a and 4b an should be compared to the diagram of the MIE type devices in FIG. 3. This device has a channel 30 of rectangular section, one wall of which is constituted by a polarizable interface 31. A first electrode 32 is disposed at one end of the microchannel and a second electrode 33 is disposed at its other end, these electrodes being connected to means 34 for generating and controlling a voltage difference between them. A third electrode 35 is disposed at one end of the polarizable interface 32 and a fourth electrode 36 is disposed at its other end, these electrodes being connected to means 37, 38 for generating and controlling a voltage difference between them.

Figure 6:
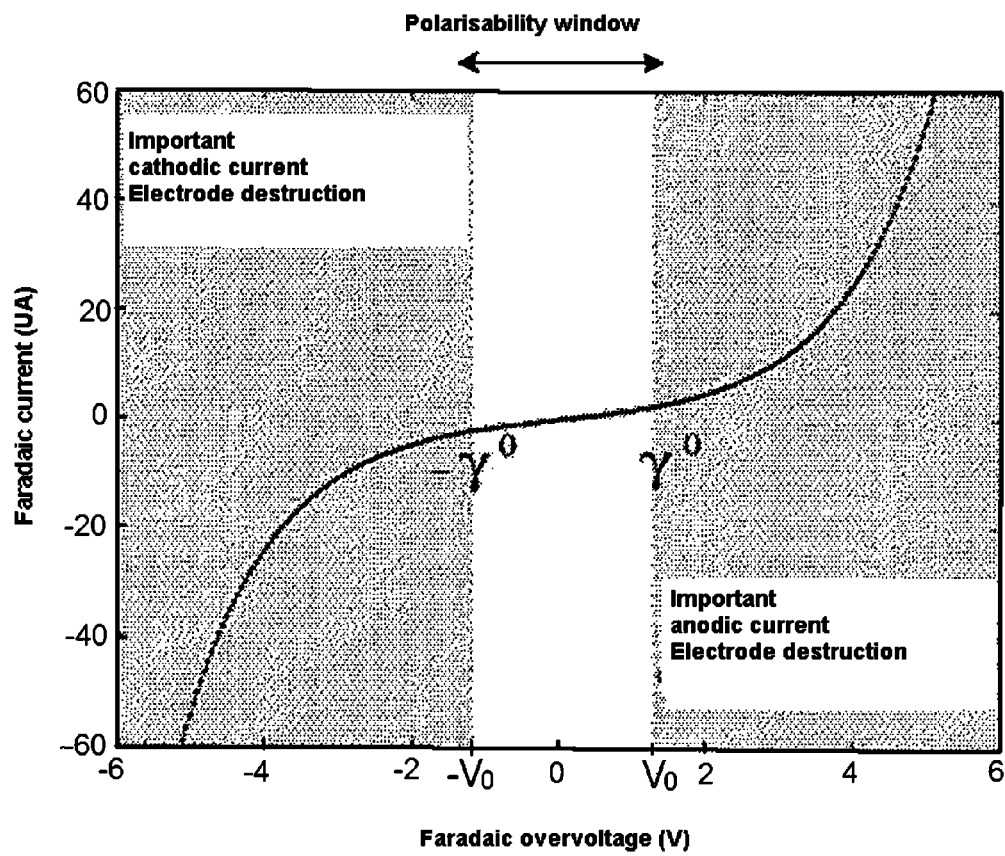
FIG. 6 shows, for a polarizable material, the curve of the faradaic current versus the overvoltage applied thereto.

As stated above, this polarizable interface has a very weak faradaic current when an overvoltage in a polarizability is applied to it, namely as long as $/V-\Phi/<V_o$, where V is the potential in the polarizable interface, $\Phi$ is the potential of the liquid in contact with this interface, and $V_0$ is the overvoltage above which the faradaic current increases rapidly as shown in FIG. 6.

In this configuration, one must thus be sure to impose an electric potential at the interface so that the faradaic overvoltage remains in the polarizability range at all points of the interface. In the case of the rectilinear microchannel 30 filled with an electrolyte through which a large potential drop is imposed, it is thus essential to also ensure a potential drop through the polarizable interface. This is possible only if the interface potential is imposed at both ends of the channel, which is accomplished with the aid of the third and fourth electrodes 35, 36 and the associated means 37, 38.

By imposing for example an equivalent overvoltage at both ends, and in the case of an ideally polarizable interface (negligible current between the liquid and the interface), this overvoltage will be constant all along the channel. This configuration then enables a diffuse layer and constant electroosmotic mobility to be obtained all along the microchannel. Moreover, the variation in surface potential is no longer limited by the insulating layer so that strict equality between the variation in surface potential and overvoltage is found, always in the case of a negligible Stern layer capacitance:

$$\Delta\zeta(x)=\gamma(x)=V(x)-\phi(x)$$

Figure 7:
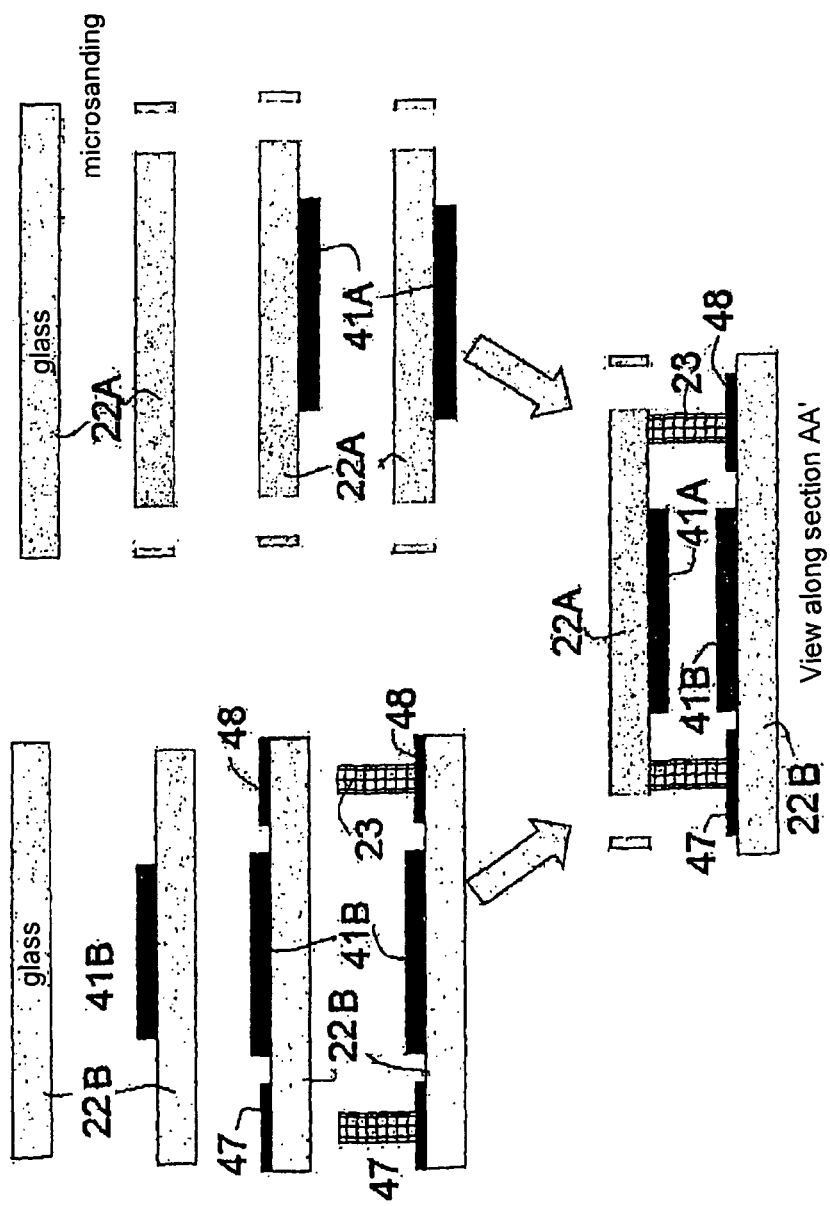
FIGS. 7a and 7b show an example of manufacturing a second variant of the invention embodiment known as "microfluidic Wheatstone bridge."

FIG. 7a shows a microfabrication technique for creating a microfluidic network according to the invention in which only part of the network is subject to surface potential control with the aid of polarizable interfaces. This technique, known as glass-PDMS-glass, is described in particular in the following reference: Plecis, A. and Y. Chen, Fabrication of Microfluidic Devices Based on Glass-PDMS-Glass Technology. *Microelectronic Engineering*, 2007, 84(5-8): pp. 1265-1269. Here, two rigid substrates are used to define the upper and lower walls of the microfluidic network. The upper substrate is first pierced by a microsanding technique to allow access to the fluidic network as well as any connection zones with the electrode network.

Figure 7B:
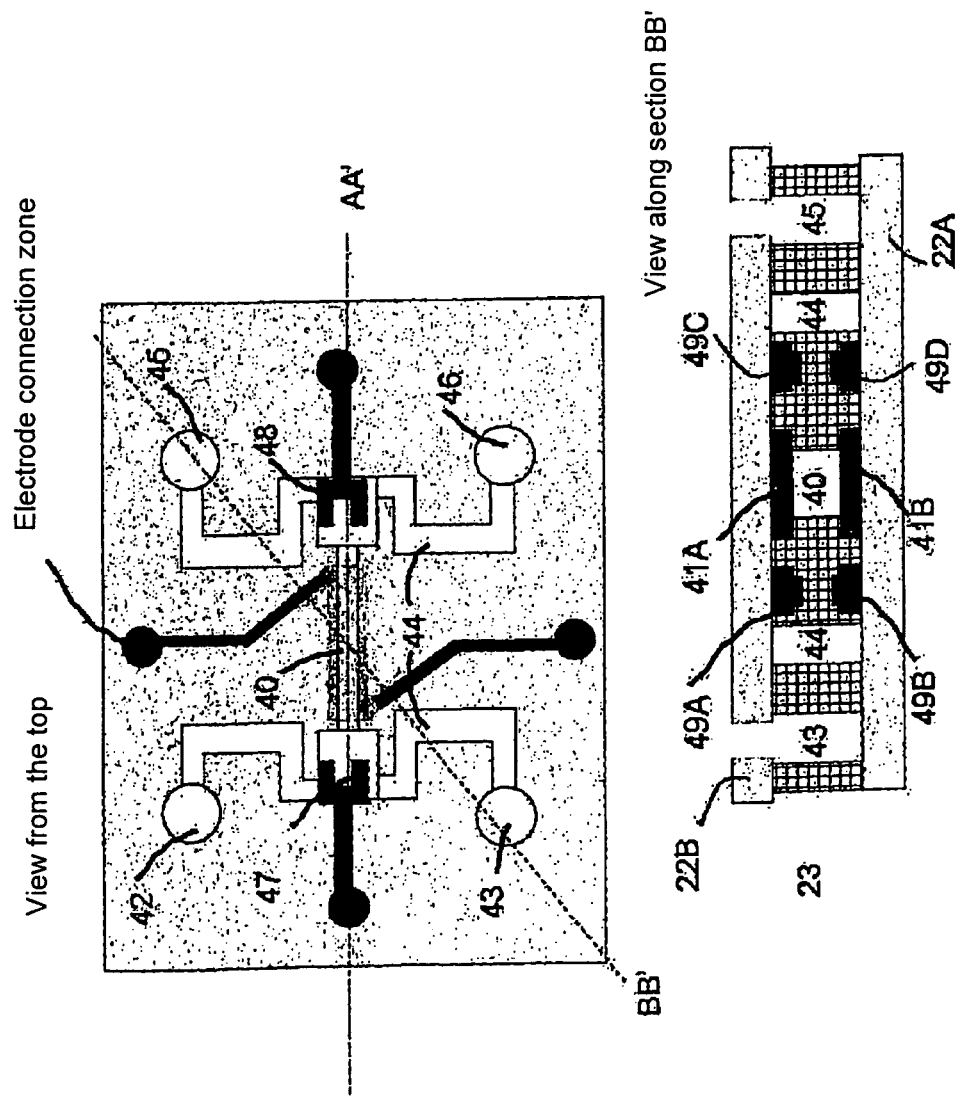

A polarizable material 41A, 41B (conducting SiC or CNx) is first structured on the upper $22_1$ and lower $22_2$ glass substrates by classical deposition/etching or liftoff techniques shown in particular in FIG. 4a. In the next step, a network of metal electrodes is aligned on these interfaces. As shown in FIG. 7b which shows a device according to one embodiment of the invention known as "microfluidic Wheatstone bridge" which uses the technique shown in 7a, this network has: (i) current electrodes 47, 48 for imposing a certain electric potential on the liquid (only on the lower substrate); (ii) control electrodes 49A, 49B, 49C, 49D for imposing the electric potential at the polarizable interface. The microfluidic network is then made with the aid of a casting step that enables a thin (typically 5 to 10 µm) layer of PDMS 23 to be structured. It is also possible to use a photosensitive silicone resin (for example Dow Corning WL-5150) to make the fluidic network. The typical dimensions for the central channel 40 are for example 4250 µm in length and 300 µm in width. The upper and lower substrates are then glued after alignment, producing a microchannel 40 more than 95% of inside surface of which is composed of a polarizable network whose surface potential can be controlled.

Thus, this device constituting a chip has a microchannel 40 of rectangular section whose upper and lower walls are made of a polarizable interface, 41A and 41B respectively. One end of this microchannel is connected to two reservoirs 42, 43 via connecting channels 44 while the other end of the channel is connected to two reservoirs 45, 46 via connecting channels 44. A first electrode 47 is disposed at one end of the microchannel and a second electrode 48 is disposed at its other end; these electrodes are made on the lower substrate 22B and connected to external means not shown for generating and controlling a voltage difference between them and able to generate a longitudinal electric field, also called transverse electric field, through the central microchannel 40. Two electrodes 49A and 49B are connected respectively to the left end of the polarizable interface on the lower and upper substrates 41A and 41B. Two other electrodes 49C and 49D are connected respectively to the right end of the polarizable interface on upper and lower substrates 22A and 22B, respectively. These electrode pairs 49A and 49B on the one hand and 49C and 49D on the other hand are connected to external means (not shown) for generating and controlling an electric potential.

This type of device enables the electroosmotic flow and hence the surface potential to be measured in the presence of an electric field through the microchannel 40 located in the center of an "H" structure, the reservoirs being located at the free ends of the branches of the H. The electroosmotic flow measurement principle is described in particular in Plecis A., Chen Y. "Microfluidic analogy of the Wheatstone bridge for systematic investigations of electro-osmotic flows". Analytical Chemistry 2008, 80(10), 3736-42. Its function is to study the properties of the polarizable interfaces and validate the feasibility of these devices.

Figure 8:
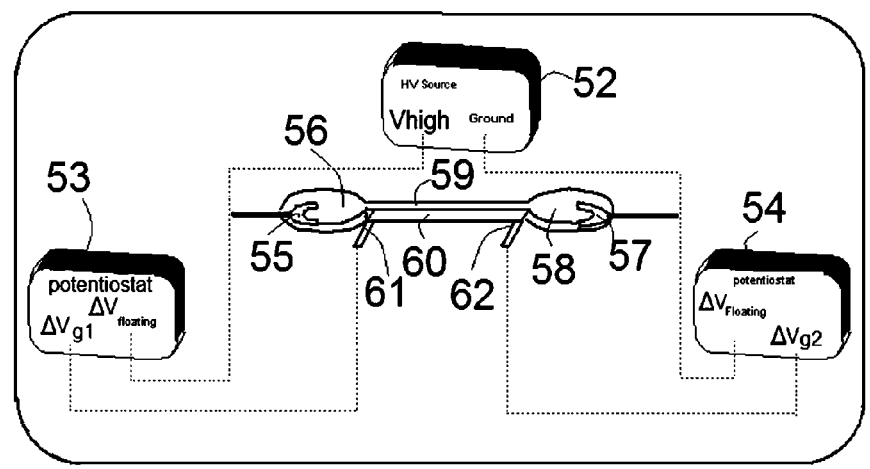
FIG. 8 shows an example of an external electric assembly associated with the device of FIGS. 7a and 7b and requiring a first, a second, and a third external voltage source.
Figure 9A:
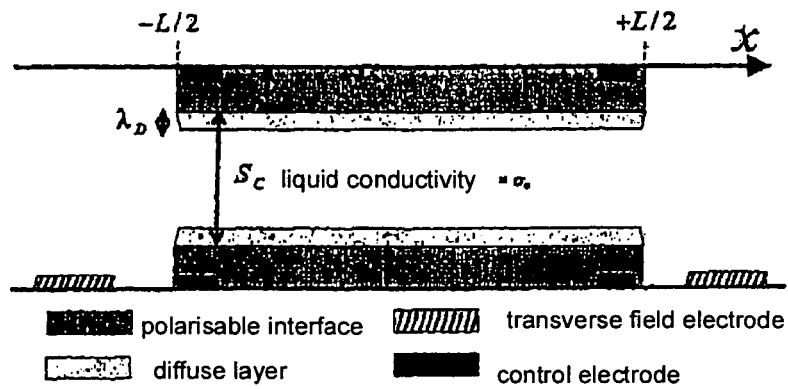
FIGS. 9a, 9b, and 9c show different parameters, namely the geometry, distribution of electric potentials, and distribution of electric currents, measured from a device according to FIGS. 7a and 7b.
Figure 9B:
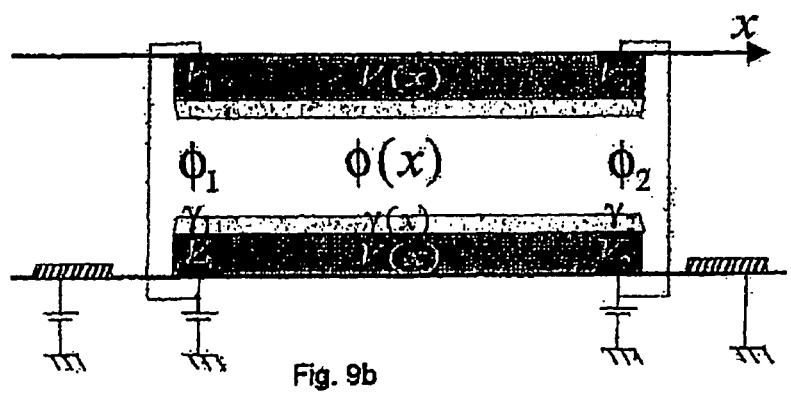
Figure 9C:
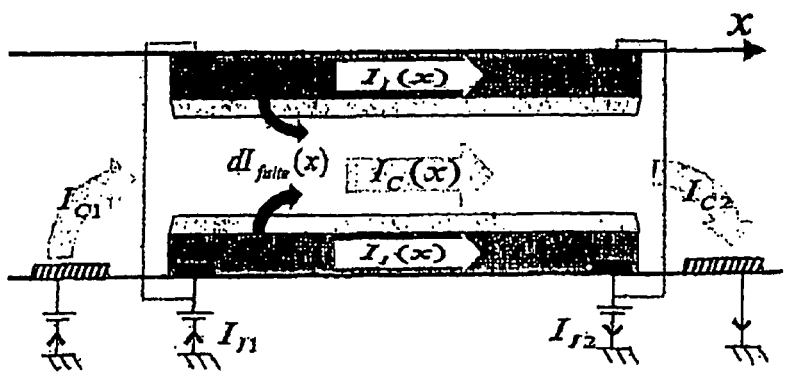

FIG. 8 shows an example of an external electrical assembly associated with the device of FIGS. 7a and 7b and requiring a first, a second, and a third external voltage source 52, 53, 54. The first source 52 is connected to a first electrode 55 disposed in a first reservoir 56 and to a second electrode 57 disposed in a second reservoir 58, these reservoirs being separated by a microchannel 59 whose two parallel walls are each comprised of a polarizable interface 60 one of whose ends is connected to a third electrode 61 and the other end being connected to a fourth electrode 62. This first source is able to control the potential in the liquid contained in the reservoirs and the microchannel, while the second and third sources 53 and 54 are able to control the electric potential in the polarizable interface 60, relative to the potential in the liquid. In this configuration, the various parameters, namely the geometry, distribution of electric potentials, and distribution of electric currents are presented in FIGS. 9a, 9b, and 9c respectively.

Here we are interested in the overvoltage $\gamma=V-\Phi$ developing along the channel, because this is what gives information on the local surface potential. If no current develops at the interface (in the case of an ideally polarizable interface), the electric currents $I_I$ in the polarizable material and $I_c$ in the channel remain constant all along the microchannel. There results from Ohm's law a linear variation in potential in these two media having a conductivity $\sigma_1$ and $\sigma_c$ and a section $S_I$ and $S_C$ for the polarizable material and the channel respectively:

$$I_C = -\sigma_C S_C \frac{\partial \Phi}{\partial x}$$

$$I_I = -\sigma_I S_I \frac{\partial V}{\partial x}$$

In this ideally polarizable case, the overvoltage has a linear variation along the channel (difference of two linear potentials) and if the overvoltages applied to the two ends are equivalent ($\gamma_1=\gamma_2$), this overvoltage is constant along the microchannel (FIG. 9d).

On the other hand, if the current at the interface is no longer negligible, the electrons present in solution (respectively in the interface) will be able to pass through the interface to encounter a weaker electric potential. Their arrival or departure en masse will have the result of modifying the current in each electric "vein" and the potentials V and $\Phi$ will no longer have a linear variation. We will now present the curve of this overvoltage when the leakage current is no longer negligible.

In the case of a non-negligible faradaic current, we model this exchange current and its influence by three equations, two of which describe the conservation of the current. The third equation corresponds to the electron transfer dynamic as a function of the overvoltage. Here, a symmetrical Tafel type transfer kinetics was chosen to describe qualitatively the system:

$$dI_{leakage} = \frac{\partial I_C}{\partial x}$$

$$dI_{leakage} = \frac{\partial I_I}{\partial x}$$

$$dI_{leakage} = I_0 \sinh\left(\frac{V-\phi}{\gamma_0}\right) = I_0 \sinh\left(\frac{\gamma}{\gamma_0}\right)$$

By combining the above equations and the ohmic drop equation, we obtain the equation that governs the overvoltage in this system:

$$\frac{\partial^2 (\gamma')}{\partial x^2} = \frac{1}{L_\gamma^2} \sinh(\gamma')$$

$$\gamma' = \frac{\gamma}{\gamma_0}; L_\gamma^2 = \left(\frac{1}{S_c \sigma_c} + \frac{1}{S_t \sigma_t}\right) \frac{I_0}{\gamma_0}$$

where $\gamma'$ is the adimensional overvoltage (related to the faradaic overvoltage $\gamma_0$) and $L_\gamma$ is a parameter that has the dimension of a length.

Figure 10:
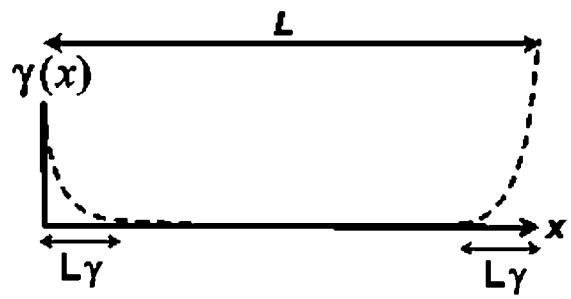
FIG. 10 shows the pattern of the overvoltage along the microchannel for a control length that is short relative to the length of the channel for a device according to FIGS. 7a and 7b.

FIG. 10 shows the shape of the overvoltage along the microchannel 60 for a small control length relative to the length of the channel for a device according to FIG. 8.

When this typical length is less than the total length of the microchannel, the overvoltage tends to disappear in the middle of the structure whatever the overvoltage imposed across the system. Hence this control length must be maximized to optimize the surface potential control in such a system. From the above equation we can extract the expression for the control length $L_\gamma$:

$$L_\gamma = \sqrt{\frac{\gamma_0}{I_0\left(\frac{1}{S_I \sigma_I} + \frac{1}{S_C \sigma_C}\right)}} = \sqrt{\frac{R_t}{(R_I + R_C)}}$$

$$R_t = \frac{\gamma_0}{I_0}; R_I = \frac{1}{S_I \sigma_I}; R_C = \frac{1}{S_C \sigma_C}$$

We see here that this length depends on the ratio between the transfer resistance at the interface $R_t$ (which determines the amplitude of the faradaic current) and the sum of the transverse resistances associated with the polarizable material $R_I$ and with the channel $R_c$ (which dictate the amplitude of the transverse currents developing there, respectively).

When this transfer resistance becomes small relative to the transverse resistances, the control length decreases, i.e., the electron transfer is sufficiently large between the two longitudinal current "veins" to quickly cancel out the potential difference between the liquid and the interface. In this case, the control is effective only over a short distance at the two ends of the channel.

Figure 11:
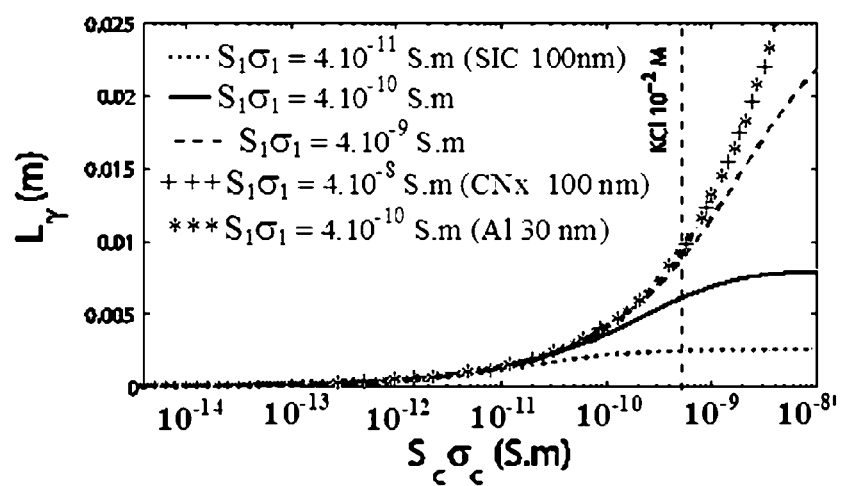
FIG. 11 shows the typical curve of the control length as a function of the ion concentration in the electrolyte and of the conductivity of the interface for interfaces with conducting SiC, in this case SiCxHy and CNx interfaces.

FIG. 11 shows the typical curve of the control length as a function of the ion concentration in the electrolyte and the conductivity of the interface for interfaces with conductive SiC, in this case in SiCxHy and CNx whose conductivities were deduced from measurements made on the devices before they were immersed in liquid. The ratio was considered fixed in the context of all these curves and corresponds to that of the conductive SiC. In this calculation, the transfer resistance ($\gamma_o/I_0$) was taken as a constant for all the interfaces. In order to obtain a realistic value for the control length, the average value of the overvoltages and cathodic and anodic faradaic currents obtained upon characterization of the conductive SiC interface cyclic voltammetry were used. Several clear trends emerge from this calculation. The first is that the typical length (hence EOF control) increases with the conductivity of the electrolyte. The second finding is that the typical control length can be limited, at high concentrations, by the resistance of the polarizable material as shown by the curves corresponding to the conductive SiC interfaces.

This relationship is found in the expression of the typical control length given above: in the first case, $R_c \gg R_I$ and the typical control length tends to zero when $R_c$ tends to infinity. In the second case, $R_I \gg R_c$ and the typical length tends to a constant that depends on the conductivity of the polarizable material.

FIGS. 12a to 12d show schematically the potential that develops in the liquid and in the interface, on the one hand a control length less than the total channel length and for the three types of regimens referred to above which depend on the relative conductivity of the two electric veins, and on the other hand for a control length greater than the total channel length.

Figure 12A:
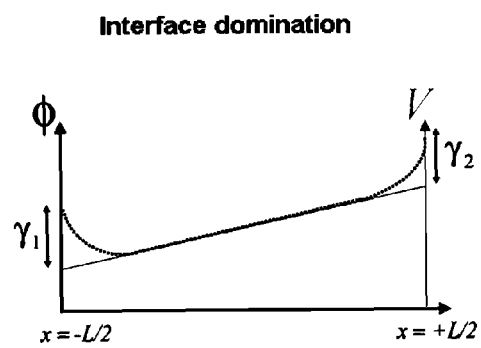
FIGS. 12a and 12d show schematically the potential that develops in the liquid and in the interface respectively, on the one hand for a control length less than the total length of the channel and for three types of different regimes and on the other hand for a control length greater than the total channel length.

When the ionic conductivity of the liquid decreases, the faradaic current becomes large with respect to the current that develops in the liquid "vein." Since the number of charge carriers is small in the channel, it takes only a few microns for the charge carriers coming from the interface to modify the electric potential in the liquid. The latter then becomes aligned on the electric potential in the interface: it is an interface domination regimen as shown in FIG. 12a.

Figure 12B:
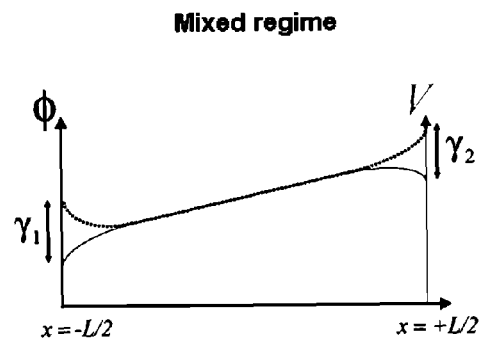

When the ionic concentration of the electrolyte is increased, $R_I$ and $R_c$ become of the same order of magnitude. There is then no domination of the interface over the liquid or vice versa. A mixed regimen is instituted, as shown in FIG. 12b, and the electrons exchanged between the two current "veins" simultaneously change the potential in the liquid and in the interface. The latter become mutually aligned on an intermediate value.

Figure 12C:
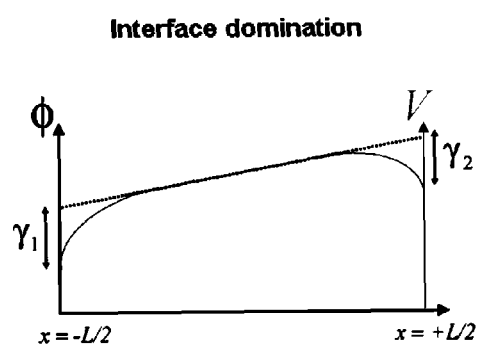
Figure 12D:
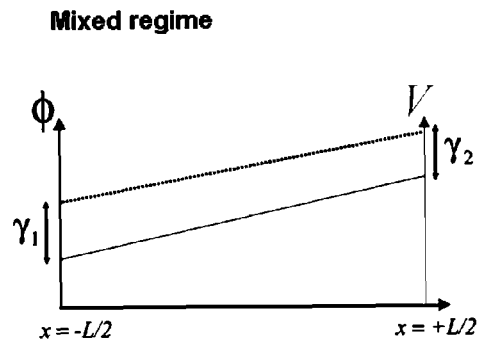

With high ionic conductivity, on the other hand, it is the conductivity of the interface that can become limiting. This case is observed in particular for the conductive SiC interface which has the lowest conductivity of the materials shown in FIG. 11. In this case, it is the liquid that has the largest reservoir of charge carriers. Hence it is this liquid that establishes the electric potential in the interface and a liquid domination regimen is obtained as shown in FIG. 12c.

In the case where the control length is not sufficient to preserve a constant overvoltage along the channel, it is obviously the liquid domination regimen which is of interest, because it concerns the strongly ionic electrolytes, which are principally used in bioseparation, and because it is at the origin of a negligible faradaic current for the solution not bringing about any noteworthy change in composition. Moreover, the transverse electric field will remain constant in the liquid all along the microchannel.

To obtain this optimal control regimen, one can thus increase the transverse electric currents as we have just discussed. Maximizing the transfer resistance between the interface and the liquid is however a second way of increasing the typical control length. If one is compelled to operate at a weak ionic strength, this strategy would even be indispensable.

Figure 13:
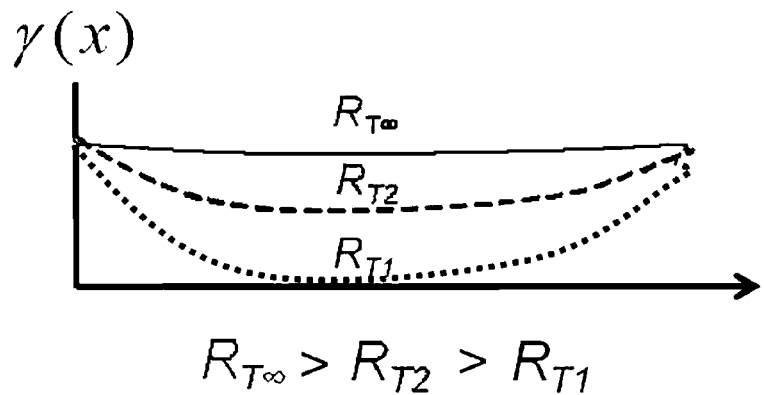
FIG. 13 shows the curve of the overvoltage obtained along the microchannel of FIGS. 7a and 7b when the transfer resistance is increased.

FIG. 13 shows the curve of the overvoltage obtained along the microchannel when the transfer resistance is increased. An ideally polarizable interface, namely one whose transfer resistance is considered to be infinite ($R_{T\infty}$) enables a constant overvoltage to be maintained all along the interface. For a given electrolyte conductivity and a sufficiently conductive interface, it is this parameter that must be maximized to improve electroosmotic flow control.

Figure 14:
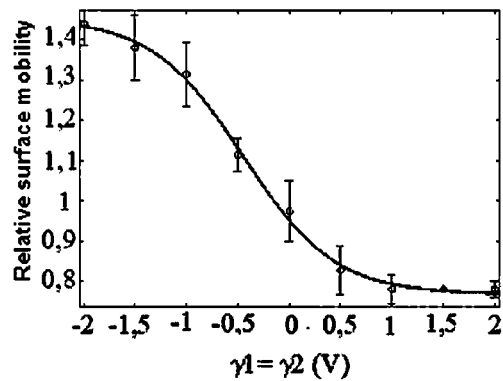
FIG. 14 shows an example of the control obtained for overvoltages less than 2 V absolute value for a SiCxHy interface and an electrolyte made of KCl (1 mM).

Thus, it proved possible in the case of the system shown in FIG. 8 to obtain EOF control for overvoltages applied at the two equivalent ends ($\gamma_1 = \gamma_2 = \gamma$). FIG. 14 shows an example of control obtained for overvoltages less than 2 V in absolute value for a conducting SiC interface and an electrolyte composed of KCl (1 mM).

Figure 15:
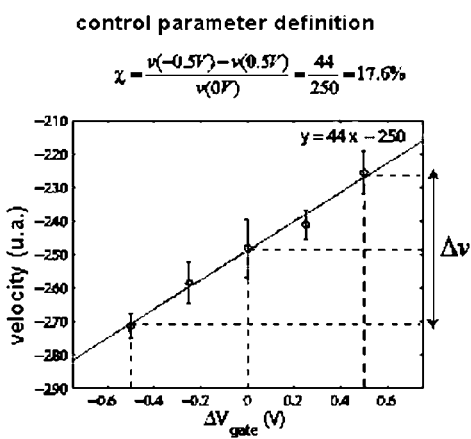
FIG. 15 shows a control example where $\chi$=17.6% for a CNx interface and a KCl (10 µM) electrolyte.

When the overvoltage is held between −0.5 V and +0.5 V, electroosmotic flow control is linear and we can define an adimensional control factor $\chi$ from this linear variation as:

$$\chi = \frac{\Delta v}{v_0}$$

where $\Delta v$ corresponds to the change in electroosmotic velocity for an overvoltage change of 1 V and $v_0$ is the velocity of the interface for a zero overvoltage. FIG. 15 shows a control example where $\chi \approx -17.6\%$ for a CNx interface and a KCl (10 μM) electrolyte.

With higher-conducting electrolytes it is possible to achieve control factors of more than 100% and thus to reverse the direction of the EOF.

Figures 16A, 16B:
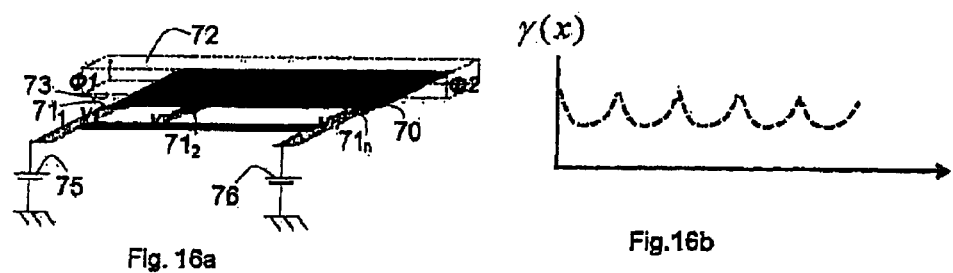

FIG. 16a shows a third embodiment of the arrangement of a polarizable interface 70 and its associated electrode network $71_1, 71_2, \ldots, 71_n$, with a microchannel 72. A voltage generator 74, 75 is associated with each of the end electrodes $71_1$, and $71_n$, the polarizable interface 70 constitutes part of the lower wall 73 of the microchannel 72 and the electrodes are disposed transversely under the interface and in an axis perpendicular to that of the channel axis. FIG. 16b shows the curve of the overvoltage $\gamma$ along the microchannel 72, the potential in the polarizable interface being sustained by the electrode network contrary to the configuration in FIG. 13.

Figure 17:
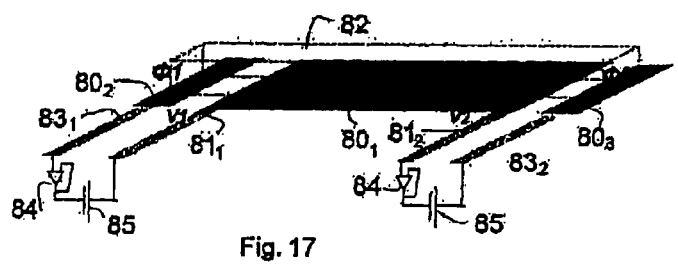
FIG. 17 shows the arrangement of a main polarizable interface and two secondary polarizable interfaces used as reference electrodes in the context of a fourth embodiment of the invention.

FIG. 17 shows a fourth embodiment of the arrangement of a main polarizable interface $80_1$ and secondary polarizable interfaces $80_2$, $80_3$ located at opposite ends of the main interface $80_1$. These interfaces constitute part of one of the walls of a microchannel 82. A network of two electrodes $81_1$, $81_2$ is associated with the main interface $80_1$. Also, a reference electrode, $83_1$, $83_2$ respectively, is associated with each of the secondary polarizable interfaces $80_2$, $80_3$, these electrodes being able to measure the voltages Φ1 and Φ2 of the liquid in the microchannel 82 at each of said ends. Each of the reference electrodes is connected to one of the electrodes associated with the main polarizable interface by means of a follower device 84 and a voltage generator 85. All these electrodes are disposed transversely under the interface and in an axis perpendicular to that of the channel axis.

Figure 18:
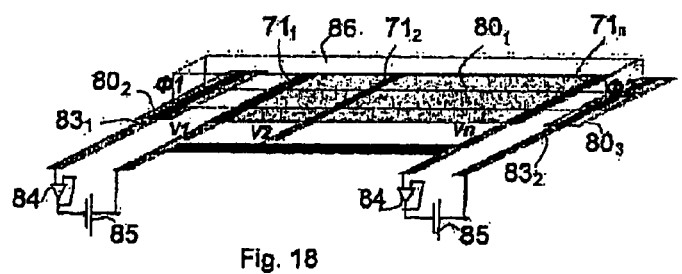
FIG. 18 shows the arrangement of a main polarizable interface and two secondary polarizable interfaces according to a fifth embodiment.

FIG. 18 shows a fifth embodiment of the arrangement of a main polarizable interface $80_1$ and two secondary polarizable interfaces $80_2$, $80_3$ located at opposite ends of the main interface $80_1$. These interfaces constitute part of one of the walls of a microchannel 86. An electrode network $71_1, 71_2, \ldots, 71_n$ is associated with the main interface $80_1$. In addition, a reference electrode, respectively $83_1$, $83_2$ is associated with each of the secondary polarizable interfaces $80_2$, $80_3$, these electrodes being able to measure the voltages Φ1 and Φ2 of the liquid in the microchannel 82 at each of said ends. Each of the reference electrodes is connected to one of the electrodes associated with the main polarizable interface through a follower device 84 and a voltage generator 85.

In this embodiment, the electrodes are positioned above the polarizable interface that is associated with it, and are in direct contact with the liquid, contrary to the previous embodiments.

Figure 19:
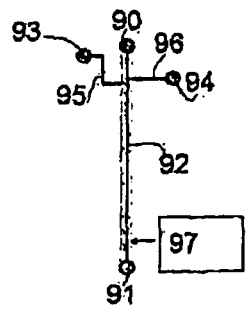
FIG. 19 shows an application example of a device according to the invention to an electrophoretic separation column in a chip separation system of known geometry.

FIG. 19 shows one application example of a device according to the invention with an electrophoretic separation column in a chip separation system of known geometry. This column has a first and a second reservoir 90, 91 which are separated by a rectilinear separation microchannel 92. A third and a fourth reservoir 93, 94 are disposed near said first reservoir 90 and are connected to said separation microchannel 92 respectively by a double-bent microchannel 95 and by a rectilinear microchannel 96. The section of the separation microchannel is rectangular and at least one of its walls, possibly two, is covered with or comprised of a layer of polarizable conductive material constituting a polarizable interface 76 able to come in contact with a fluid circulating in the separation microchannel 92. Analyte detection means 97, comprised for example of a camera, spectroscopy means, fluorescence analysis means, etc., are positioned opposite the separation channel, near the second reservoir 91.

Figure 20A:
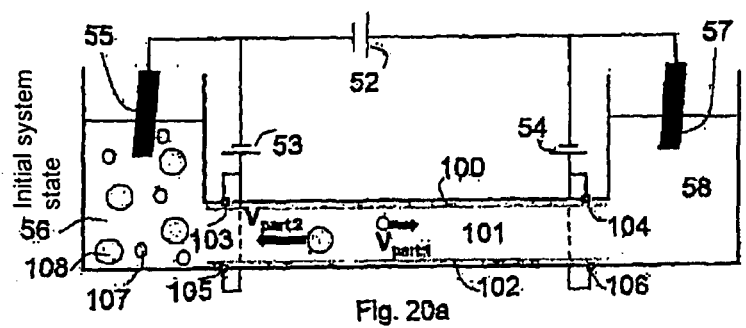
FIG. 20 shows an application example of a device according to the invention as an electrophoretic gate.
Figure 20B:
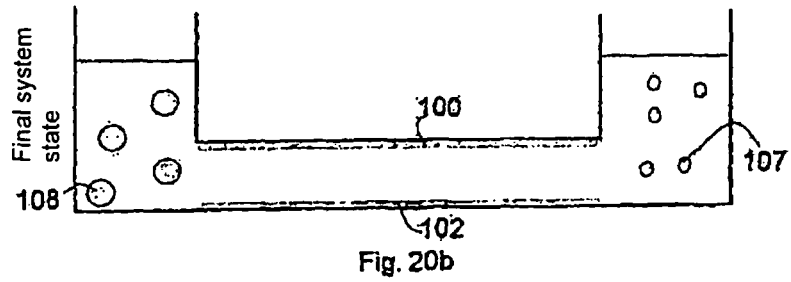

FIG. 20 shows an application example of a device according to the invention as an electrophoretic gate, which greatly simplifies the geometry of the existing electrophoretic separation columns. The device used is that of FIG. 4 except that the fabrication technique used is the glass-PDMS-glass technique described above and allows the polarizable interfaces to be made of a first coating 100 disposed on the inside face of the lower wall of a microchannel 101 and by a second coating 102 disposed on the inside face of the upper wall of microchannel 101, these coatings being connected to an associated network of electrodes 103, 104, 105, 106 themselves connected to voltage generators 52, 53 54.

The option of choosing the electroosmotic flow (EOF) independently of the transverse field also opens up further prospects for electrophoretic separation: it is possible to choose, independently of the transverse electric field, the counterflow value that the molecules must encounter to pass through the microchannel. When a sufficient EOF resists electrophoretic migration, transport of the slowest molecules can be stopped and one may then obtain the result shown in FIG. 20b with the molecules 108 remaining in the first reservoir 56 in which they were initially located while the molecules 107 with higher electrophoretic mobility pass through the microchannel 101 until they reach the second reservoir 58.

Figure 21:
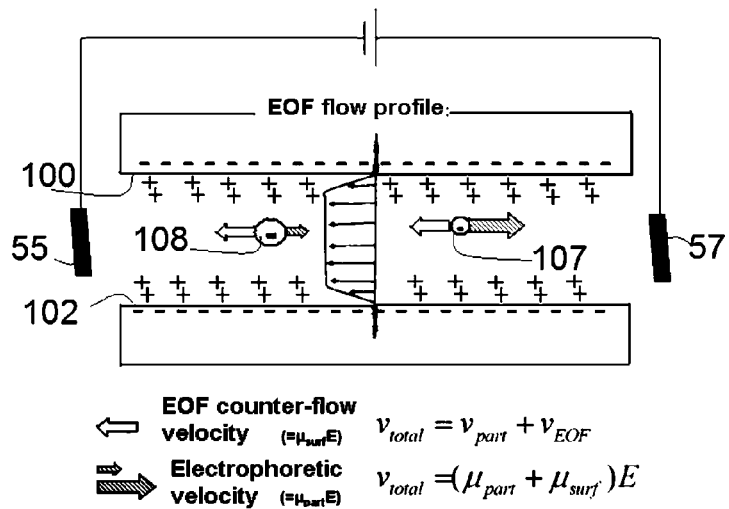
FIG. 21 explains the separation process of analytes contained in an electrolyte with an electrophoretic gate according to FIG. 20.

This phenomenon is illustrated in FIG. 21. The left molecule 108 does not have enough electrophoretic velocity to "fight" the EOF. Its overall velocity is negative in the microchannel. The right molecule, on the other hand, has sufficient electrophoretic mobility to pass through the EOF. It is carried from the left reservoir 56 to the right reservoir 58.

It will be recalled that the velocity of a charged particle, subjected to a transverse field, is proportional to the latter. The total mobility of the particle is the sum of is own mobility and the surface mobility. Thus, if the particle has greater electrophoretic mobility than the converse of the surface mobility, it will have a total positive velocity: it is carried by the channel. If, on the other hand, its own mobility is too low, its velocity within the microchannel will be negative. This molecule is not carried. The microchannel then acts as an electrophoretic gate because it lets through only a range of electrophoretic mobilities higher than a critical mobility.

Figure 22:
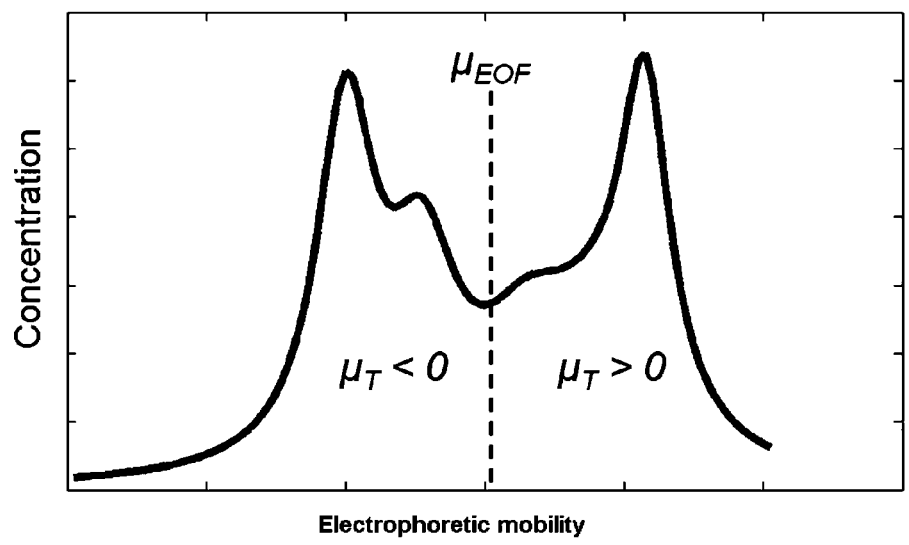
FIG. 22 gives an example of the concentration of species present in a biological specimen as a function of their electrophoretic mobility.

Taking a biological specimen in which the species present have a concentration as a function of their electrophoretic mobility such as that shown in FIG. 22, a device such as that of FIG. 20 enables the biological specimen to be separated into two sub-specimens with different electrophoretic spectra. Depending on the direction of the electric field, one or the other of the electrophoretic ranges will be carried through the microchannel.

The cutoff mobility $\mu_{EOF}$ is hence defined by the surface mobility. It can be changed at will using the polarizable interfaces. It thus becomes possible to separate a specimen into two sub-specimens with different mobility distributions. For a given electric field, only a range of molecules with be carried through the microchannel. One need only change the sign of the transverse field without changing the surface mobility for the order relation to be reversed and the other range of mobilities will be carried instead.

For a given (non-zero) particle voltage v, it can be shown that the transport coefficient $J_0$ through a channel with section S and length L obeys the equation:

$$J_0 = \frac{C_0 v S}{1 - e^{-vL/D}}$$

Figure 23A:
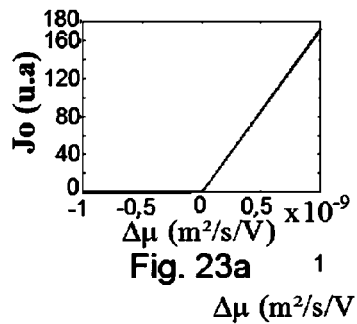
FIGS. 23a and 23b show the curve of the flow as a function of the mobility difference $\Delta\mu$ relative to the cutoff mobility for a channel 1 mm long.
Figure 23B:
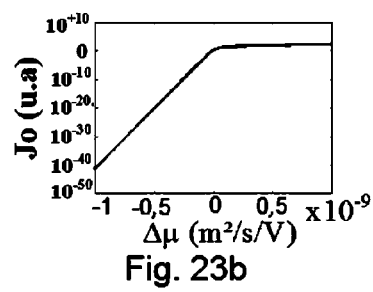

This transport coefficient change was calculated as a function of the difference in mobility μL relative to the cutoff mobility for a channel of length 1 mm, a diffusion coefficient of $10^{-10}$ m²/sec, and an electric field of 100 V/cm (10 V through the gate); one then obtains the flow represented linearly and logarithmically in FIGS. 23a and 23b respectively.

The electrophoretic gate functions as a high-pass or low-pass filter (if the transverse field is reversed). Its cutoff is very clean because we see a decrease in the transport coefficient of one decade every 0.02 μm/sec/(V/cm). This is a mobility difference that is difficult to discriminate in classical capillary electrophoresis. This type of device constitutes an elementary fractionation system that can be used as the basic cell of a more complex fractionation system.

Figures 24A, 24B:
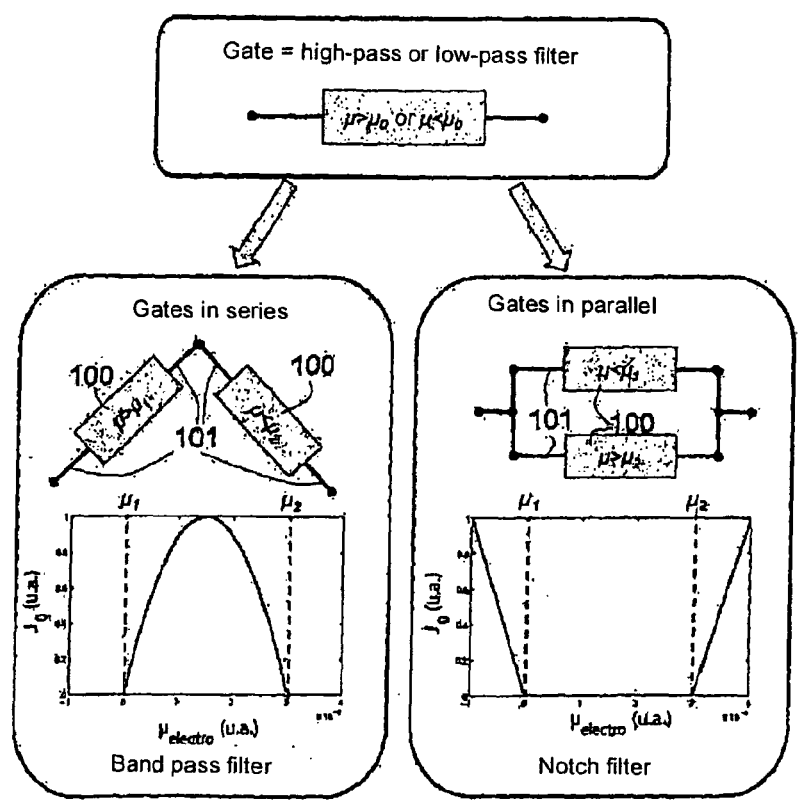
FIGS. 24a and 24b show the association of two electrophoretic gates disposed in series and in parallel, respectively.

As shown in FIGS. 24a and 24b, two electrophoretic gates can be associated in parallel or in series in order to perform the electrophoretic sorting function of the band-pass or notch type. In the case of two electrophoretic gates in series, a band-pass filter is obtained. With this type of system, it is possible to monitor the presence of an electrophoretic range in a specimen continuously. In the case of two electrophoretic gates in parallel, a notch filter is obtained. It is then possible to filter an electrophoretic range contained in an initial specimen. It is possible to increase the number of electrophoretic gates substantially.

Figure 25A:
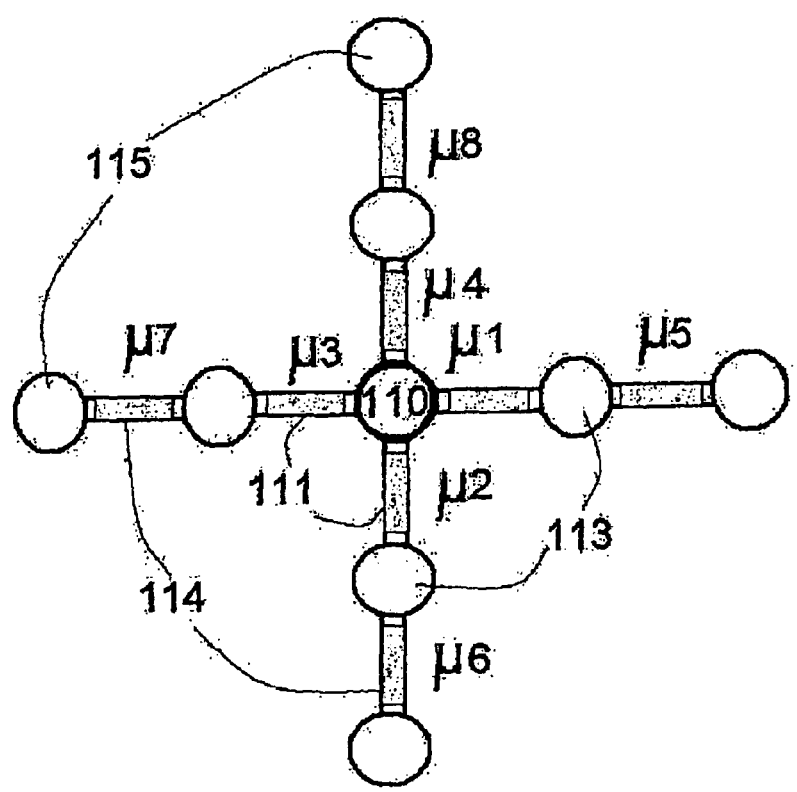
FIGS. 25a to 25c are simplified diagrams of complex systems with electrophoretic gates according to the invention.
Figure 25B:
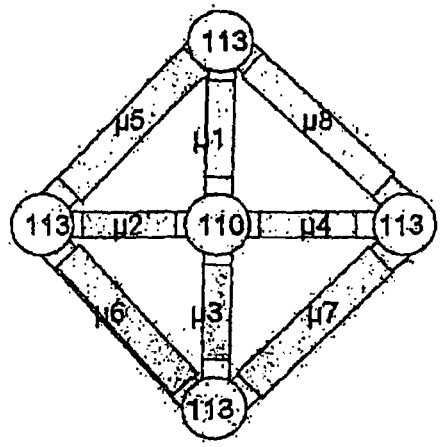
Figure 25C:
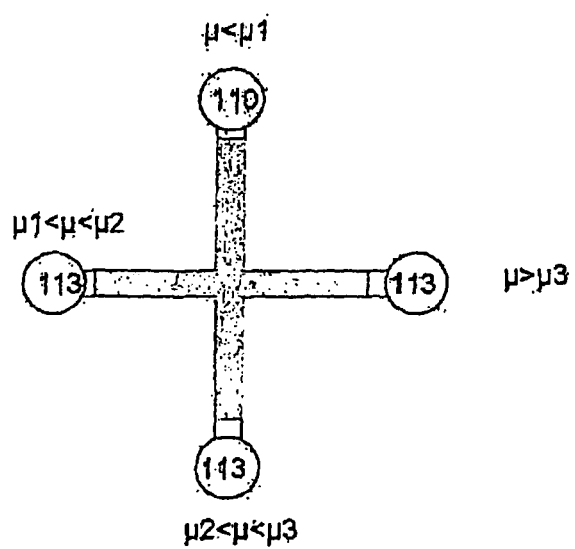

FIGS. 25a to 25c are simplified diagrams of a device having a central reservoir 110 designed to receive a specimen to be analyzed and connected, in this embodiment, to a complex system of electrophoretic gates. In FIG. 25a, each network is composed, starting from said central reservoir, of a first channel 111 whose other end is connected to a second reservoir 113 itself connected to a second microchannel 114 itself connected to a third reservoir 115.

Each of the first and second microchannels 111 and 114 has at least part of one of its walls coated interiorly or composed of a conducting and polarizable material, for example a very fine layer (1 nm) of aluminum, this material being connected to an electrode network, not shown, made of platinum for example (50 nm); these are in turn connected to means, not shown, for controlling the electric potential. These interfaces are thus able to control the surface potential independently of each other in the microchannels 111 and 114. Also, electrical and/or mechanical means, not shown, are able to generate a potential difference or a pressure gradient between the various reservoirs 110, 113, and 115.

By controlling the various voltages and possibly the pressures, it is possible to obtain a cutoff mobility μ1 to μ8 that is specific to each of the first and the second microchannels, thus enabling the initial specimen to be fractionated, in this embodiment, into 9 subgroups of molecules with different electrophoretic mobility distributions.

It is of course possible to increase the number of electrophoretic gates and reservoirs indefinitely and to connect several reservoirs in the form of a cross-network as shown in FIG. 25b.

Finally, the properties of the electrophoretic gates are modifiable simply by changing the voltage settings: a given network of electrophoretic gates can allow a multitude of functions without the chip having to be changed. Such a device can also function sequentially or continuously.

FIG. 25c shows an alternative embodiment of FIG. 25a in which each of the four networks has only one microchannel 111 and a second reservoir 112. Such a device is designed to operate sequentially and separates four groups of molecules with different electrophoretic mobilities.

SEQUENCE LISTING

Not applicable

The invention claimed is:

1. A microfluidic device for separating, fractionating, or preconcentrating analytes contained in an electrolyte having at least two reservoirs separated by at least one microchannel and/or nanochannel, wherein:

said at least one microchannel and/or nanochannel has a planar geometry, at least part of the upper and/or lower wall of the microchannel is made of and/or coated interiorly with a conducting and polarizable material or group of materials constituting a polarizable interface or interface network, at least one electrode or at least one electrode network is connected at at least one point of the polarizable material or group of materials, the conductive and polarizable material or group of materials has a polarizability window being at least 0.5 V for cathodic and anodic reactions, the surface electrical conductance of said interface or interface network being equal to at least 100 nS.

2. The device according to claim 1, wherein the microchannel has n walls where n>2 and at most n−1 walls are coated with or comprised of a conducting and polarizable material or group of materials constituting a polarizable interface or interface network.

3. The device according to claim 1, wherein the material of which said polarizable interface consists includes at least one of the following materials: conducting SiC, CNx and/or HxCNy with x≠1 and y≠0, pure carbon, doped diamond, doped or undoped and crystalline or amorphous silicon, germanium, and any solid material that could be structured with the aid of standard microfabrication techniques and that could have, as an interface or interface network, a homogeneous surface conductivity greater than or equal to 100 nS.

4. The device according to claim 1, wherein a chemical treatment and/or surface grafting is applied to said polarizable interface in order to increase its polarizability.

5. The device according to claim 1, wherein the device has at least one reference electrode able to measure the electric potential of the electrolyte at a point in the microfluidic network.

6. The device according to claim 5, wherein the at least one reference electrode is composed of a part of the polarizable interface network not connected to this network and connected at at least one point to an electrode not connected to the rest of the electrode network.

7. The device according to claim 1, wherein the device has at least a first and a second electrode known as "longitudinal field" electrodes with which a voltage generator is associated, these electrodes being disposed respectively on one and the other side of at least one part of the fluidic network containing the microchannel polarizable interface network and being able to generate a change in electric potential in the electrolyte.

8. The device according to claim 7, wherein the device has at least one electrical means able to set the electric potential at at least one point in the electrode network relative to the potential of at least one of said "longitudinal field" electrodes or at least one reference electrode, namely directly connected to the latter electrode or connected to a voltage follower electrical means able to follow the potential of this reference electrode.

9. The device according to claim 1, wherein the device has at least first means for generating an overpressure in at least one of the reservoirs.

10. The device according to claim 9, wherein the at least first means for generating an overpressure in at least one of the reservoirs is also able to control the value of this overpressure.

11. A method for separating, fractionating, or preconcentrating analytes contained in an electrolyte implemented by a device according to claim 1, comprising the following steps:

filling at least one reservoir with an electrolyte and a specimen to be analyzed that contains analytes, applying at least one potential difference between at least one longitudinal or reference electrode and at least one control electrode connected at a point in the polarizable network, applying at least one potential difference at the longitudinal electrodes and/or a pressure difference at the reservoirs, with the aid of a detector, detecting the presence of analytes at at least one point of the microfluidic network.

* * * * *